US006110671A

United States Patent [19]

Kim

[11] Patent Number: 6,110,671
[45] Date of Patent: Aug. 29, 2000

[54] METHOD OF MEASURING TUMOR SUPPRESSOR GENE P53

[75] Inventor: Jerome H. Kim, Baltimore, Md.

[73] Assignee: The United States of America as represented by the Secretary of the Army, Washington, D.C.

[21] Appl. No.: 08/832,502

[22] Filed: Apr. 3, 1997

Related U.S. Application Data

[60] Provisional application No. 60/014,807, Apr. 4, 1996.
[51] Int. Cl.[7] .............................. C12Q 1/68; C12N 15/10; C07H 21/04
[52] U.S. Cl. ........................... 435/6; 435/91.2; 536/23.1; 536/24.3; 536/24.32; 536/24.33
[58] Field of Search .................................. 536/23.1, 24.3, 536/24.32, 24.33; 435/6, 91.2

[56] References Cited

U.S. PATENT DOCUMENTS 5,726,018  3/1998  Pasternack .................................... 435/6
5,811,231  9/1998  Farr et al. .................................... 435/6

*Primary Examiner*—David Guzo
*Attorney, Agent, or Firm*—Charles Harris; John Moran; Elizabeth Arwine

[57] ABSTRACT

The instant invention provides a means for quantitatively determining the level of tumor suppressor gene p53 by determination of level of messenger ribonucleic acid (mRNA) of the gene in a sample when compared with a prepared standard. The assay is quantitative in that the specific number of copies of the p53 mRNA in a sample may be derived from a curve from a standard of p53 RNA. The RNA used in preparation of a standard curve to quantitate RNA is generated using a plasmid which is part of the invention. In the assay, the RNA is produced by a protein (RNA polymerase) that reads the DNA message and manufactures an RNA copy. The RNA content of the transcribed sample is determined spectrophotometrically to measure the molar concentration. With prior knowledge of the molecular weight of the transcribed RNA and using Avogadro's number, the actual number of molecules of transcribed "control" p53 RNA can be determined

4 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: RNA (genomic)

(iii) HYPOTHETICAL: YES (iv) ANTI-SENSE: NO (xi) SEQUENCE DESCRIPTION: SEQ ID NO:1:

CATCTACAAG CAGTCACA                                                          18

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: RNA (genomic)

(iii) HYPOTHETICAL: YES (iv) ANTI-SENSE: NO (xi) SEQUENCE DESCRIPTION: SEQ ID NO:2:

GCAGTGCTCG CTTAGTGC                                                          18

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: RNA (genomic)

```
        (iii) HYPOTHETICAL: YES (iv) ANTI-SENSE: NO (xi) SEQUENCE DESCRIPTION: SEQ ID NO:3:

ATCCACTACA ACTACATG                                                      18

(2) INFORMATION FOR SEQ ID NO:4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: RNA (genomic)

(iii) HYPOTHETICAL: YES (iv) ANTI-SENSE: NO (xi) SEQUENCE DESCRIPTION: SEQ ID NO:4:

ATCATGTTTG AGACCCTTCA A                                                  21

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: RNA (genomic)

(iii) HYPOTHETICAL: YES (iv) ANTI-SENSE: NO (xi) SEQUENCE DESCRIPTION: SEQ ID NO:5:

CATCTCTTGC TCGAAGTCCA                                                    20

(2) INFORMATION FOR SEQ ID NO:6:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: RNA (genomic)

(iii) HYPOTHETICAL: YES (iv) ANTI-SENSE: NO (xi) SEQUENCE DESCRIPTION: SEQ ID NO:6:

GACCTGGCTG GCCCGGACCT GACTGACTAC TAC                                     33
```

METHOD OF MEASURING TUMOR SUPPRESSOR GENE P53

This application takes priority from Provisional Application 60/014,807 filed Apr. 4, 1996.

FIELD OF THE INVENTION

This invention relates to the field of biological assays. The instant invention provides a means for quantitatively determining the level of tumor suppressor gene p53 by determination of level of messenger ribonucleic acid (mRNA) of the gene in a sample when compared with a prepared standard.

DESCRIPTION OF THE INVENTION

The instant invention is an assay using reverse transcriptase polymerase chain reaction (RT-PCR) in an assay for p53 mRNA. The p53 is an anti-oncogene for tumor suppressor gene and is the most commonly mutated tumor suppressor gene found in human cancers. The assay is quantitative in that the specific number of copies of the p53 mRNA in a sample may be derived from a curve from a standard of p53 RNA. The RNA used in preparation of a standard curve to quantitate RNA is generated using a plasmid which is part of the invention. In the assay, the RNA is produced by a protein (RNA polymerase) that reads the DNA message and manufactures an RNA copy. The RNA content of the transcribed sample is determined spectrophotometrically to measure the molar concentration. With prior knowledge of the molecular weight of the transcribed RNA and using Avogadro's number, the actual number of molecules of transcripted "control" p53 RNA can be determined. The copy number of experimental samples is determined by comparison of the PCR-generated signal from patient peripheral mononuclear blood cells (PMBC) with the curve of PCR generated signals from serial dilutions on the standard curve.

MATERIALS AND METHODS

Blood was collected from HIV seropositive patients enrolled in the army vaccine or HIV natural history studies. Blood samples were also collected from volunteers working in the laboratory. The peripheral blood mononuclear cells (PMBC) were obtained by centrifuging the cells on Focol and removing the "buffy" coat (top layer). The cells were washed 2–3 times in Dulbecco's phosphate buffered saline. The cells were either used immediately or were frozen in media containing 10% DMSO and 20% fetal calf serum. The samples were stored in liquid nitrogen until needed.

The following oligonucleotides (information within ( ) refers to nucleotide position) have been generated:

Generally, the following procedure was followed:

Reverse Transcription of p53 mRNA 2.5 $\mu$M of the 3' p53 oligo was added to the RNA and incubated for 60 minutes at 45° C. with 25 mM dNTPs, buffer and Superscript II reverse transcriptase. The 80 $\mu$l of PCR mix containing additional dNTPs and the 5' p53 oligonucleotide were added to the PCR mix.

PCR step:

The mix was subjected to 30 cycles at varying temperatures; 95° C. for 1 minute, 57° C. for 2 minutes 72° C. for 3 minutes followed by a final 10 minutes elongation at 72° C. The products were divided into three samples, then applied onto 1.5% agarose gel and subjected to electrophoresis. The gels were then pressure blotted onto nylon filters, prehybridized from 1–24 hours, and probed with a $^{32}$P-labelled internal oligonucleotide specific for NT 819–836 of the p53 sequences. After washing, the blots were analyzed on a Molecular Dynamics PhosphorImager using ImageQuant, software developed by Molecular Dynamics of Sunnyvale, Calif.

The standard plasmid 'p53 pIC, clone 10' was created by an Nco I/Stu I digestion of the pH p53 plasmid obtained from the American Type culture Collection in Rockville, Md. The fragment containing the 564 nt of p53 sequence (cDNA) was ligated onto the pGEM-4z (Promega, Madison, Wis.). The inserted p53 fragment was sequenced to verify its correctness. The plasmid was cut with HinD III, then purified with ChemClean (Bio 101, Vista, Calif.). Three $\mu$g of plasmid was placed in transcription buffer containing 10 mM DTT, RNAsin, 0.5 mM ribonucleotide triphosphates, and SP6 RNA polymerase (Promega). The resulting mixture was incubated for 2 hours at 40° C. The 2.5 $\mu$l DNAse was added to destroy the plasmid. The mixture was extracted with a mixture of phenol, chloroform and isoamyl alcohol followed by extraction with chloroform alone. The samples were applied to a C100 spin column (Clontech Labs, Palo Alto, Calif.). The RNA concentration in the eluate was a evaluated spectrophotometrically. The length of the transcript is known. Therefore, the concentration can be used to calculate the molarity, which is then used to determine a "copy number" per $\mu$l of the sample. This standard is diluted to $1 \times 10^{10}$ copies and aliquotted for future use. It is this RNA standard that is used for copy number determinations.

The assay may be standardized for cell number by utilization of β-actin RT-PCR asn shown above. The PMBCs of an HIV-negative volunteer (prepared as described above) are carefully counted and are subjected to lysis and extraction in RNAzol B (TelTest, Friendswood, Tex.) followed by addition of rRNA (4 $\mu$g/$\mu$l). The sample is then extracted in chloroform and incubated on ice for 5 minutes. It is then placed in a covered centrifuge at 4° C. for 15 minutes at 12,000 g. The aqueous phase is transferred to a new tube and

```
5'p53                (nt 608-625)
5'-CAT CTA CAA GCA GTC ACA-3' (SEQ ID NO: 1)
3'p53                (nt 1033-1050)
5'-GCA GTG CTC GCT TAG TGC-3' (SEQ ID NO: 2)
p53 probe            (nt 819-836)
5'-ATC CAC TAC AAC TAC ATG-3' (SEQ ID NO: 3)
β-actin controls
5'-ATC ATG TTT GAG ACC TTC AA-3' (SEQ ID NO: 4)
5'-CAT CTC TTG CTC GAA GTC CA-3' (SEQ ID NO: 5)
Internal probe for β-Actin was:
5'-GAC CTG GCT GGC CGG GAC CTG ACT GAC TAC TAC-3' (SEQ ID NO: 6)
``` precipitated with isopropanol. The resulting sample is again centrifuged under the same conditions as above. The pellet obtained is washed in 70% ethanol, then pelleted again in a microfuge. This procedure is repeated once. The pellet is then resuspended in 50 µl of diethyl pyrocarbonate (DEPC) in water with 3.5 mM dithiothrietol (DTT), 2.2 mM Tris buffer, 0.9 mM $MgCl_2$, RNAsin 1.25 µl (total) and DNase 2.5 µl. The samples are incubated for 60 minutes at 37° C. The DNase is then inactivated for 15 minutes at 95–100°. The sample is cooled and 1.5 µl of RNAsin is added. The sample is divided into smaller aliquotes. These aliquots are then thawed and diluted to make the β-actin standardization curves.

The β-actin curves are used to standardize the p53 copy number. For example, the p53 assay is performed using 2000 "cell equivalents of RNA determined from the number of cells counted by means such as hemocytometer. The p53 number control curve is calculated as used to estimate the number of copies of p53 found in a sample of 2000 cells. The separate RT-PCR for β-actin can be performed on 500 cell equivalents of RNA from the sample and then compared to the data obtained from a serial dilution (100 cell equivalents to 1 cell equivalent) of RNA from a control PBMC sample. From this comparison a correction factor is obtained. For example, the β-actin data may suggest that there is only 100 cell equivalents of RNA in the sample tested rather than the 500 cell equivalents expected under the circumstances. The p53 copy number of that sample is multiplied by a factor of 5 to correct for the "deficiency" in cell number.

EXAMPLE

The cells from the HIV seronegative volunteer leukophoresis pack was utilized for the infection of CD4+ and CD8+ fractionated PBMCs. Cells from both the HIV-seropositive and HIV-seronegative donors were cultured in 20 ml of 10% fetal calf serum RPMI 1640 with 400 µl of 1000×IL-2 and phytohemagglutinin (PHA) 1 mg/ml. After washing, 1×10$^6$ cells were removed for RNA study using centrifugation at 14,000 rmp×1 minute followed by aspiration of the supernatant. The cell pellets were stored at –80° C. After 48 hours in culture, the cells were counted and separated into two 50 ml conical tubes, 30×10$^6$ cells each. Extra cells were removed for NNA, FACS (Florescence Activated Cell Sorting) and TdT assay as described below. A 500 µl sample of supernatant was placed in a microcentrifuge and centrifuged at 14,000 rpm for 1 minute, then frozen at –20° C. for later HIV p24 gag ELISA. The cells were subjected to centrifugation at 1,000 rpm for 10 minutes and the media was aspirated. half of the cells were resuspended in 1 ml of virus stock plus 1 µl of polybrene (4 µg/ml stock). The remainder were resuspended in 1 ml of 10% FCS RPMI 1640 EACH+400 µL OF 1000×IL-2 and incubated continuously at 37° continuously at 37° C. for 13 days. On days 1, 1½, 2, 4, 6, 8, 9, 11, 12, and 13 cells were harvested for RNA, endonuclease assay and TdT assay. Cells from days 6 and 13 were harvested for FACS analysis. 500 µl of supernatant was taken, centrifuged at 14,0000 rpm for 1 minute and stored at –20° C. for p24 gag ELISA. Sot volume was replaced with fresh 10% fetal calf serum RPMI 1640 and IL-2.

TdT Assay:

Cells were pelleted at 1000, rpm for 10 minutes and the supernatant was decanted. The cells were then washed once in dPBS followed by aspiration of the supernatant. The cells were resuspended in 500 µl of 1% Formalin in dPBS and incubated on ice for 15 minutes. Cells were then washed twice with dPBS and the supernatants were aspirated. The cells were resuspended in 500 µl of 75% ethanol and sorted at –20° C. until ready for flow cytometry analysis.

Flow cytometry analysis of TdT Assay samples:

After a single wash the cells were resuspended in 50 µl of terminal deoxynucleotidyl transferase (TdT) reaction mixture (0.1 M cacodylic acid, 1 mM $CoCl_2$, 0.1 mM dithiothreitol and 50 µl BSA) containing 0.t nM biotin 16 dUPT (Boehringer) and 10 units of TdT for 30 minutes at 37° C. After a wash in HBSS, 2.5 µg/ml FIC-avidin (Gibco Life Technologies, Gaithersburg, Md.) was added to a staining solution (4×SSC, 0.1% Triton X-100 and 5% non-fat dry milk) and samples were incubated for 15 minutes at room temperature.

HIV –24 levels in culture supernatant were determined using a Coulter HIV-1 p24 ELISA kit (Coulter) according to the manufacturer's specifications. A minimum value of 50 pg/ml was arbitrarily chosen as "positive".

Flow Cytometry of Mock v.s infected cells:

Five hundred thousand cells were separated into four separate 5 ml Falcon tubes and centrifuged at 1,3000 rpm for 5 minutes. The supernatant was removed and the cells were washed twice in sort buffer (1×dPBS, 1.0% BSA, 0.01% Thimerosal). Each sample was incubated with 20 µl of a monoclonal antibody against CD4, CD8, CD3 or murine IgG1. Human anti-CD4, -CD8 and -CD3 antibodies conjugated to the fluorescent marker Phycoerythrin (PE) were used. Non-specific mouse Ig conjugated to PE and fluorescein isothiocyanate (FITC) were used as controls. The cells/antibodies were incubated on ice in a rotating bath for 30 minutes. The cells and antibodies were then washed three times in sort buffer and fixed in 200 µl of 1.0% paraformaldehyde. Flow cytometry was performed to quantitate the population changes in lymphocyte subsets during the infection.

Normal PBMCs were infected using serum from HIV-infected subjects. The CD8 positive cells were subsequently removed using AIS Microselector plates according the manufacturers instructions. The percentage of remaining CD8+ cells was determined using both direct staining and cytometric analysis.

Following infection, the CD4+ and CD4++20% CD8+ cultures were investigated at several timepoints to determine the percentage of apoptotic cells. Specifically, the cells were incubated with 10 µl of 7-amino actinomycin D (7-AAD) (Sigma) using a 2 mg/ml stock solution, for 20 minutes in the dark. The cells were then analyzed directly on the flow cytometer. Apoptotic cells were distinguished by their decreased forward and increased side scatter fluorescence relative to other cells. Therefore, three populations of cells were apparent by their varying degree of fluorescence: normal live cells with normal fluorescence, apoptotic cells with dim florescence and dead cells with bright fluorescence. These criteria were used to exclude dead cells and quantify the differences between live and apoptotic populations.

EXAMPLE

RNA was isolated from cells using the RNAzol method (Teitest, Friendswood, Tex.). Cell pellets were suspended in 1 ml of RNAzol B. To this suspension, 110 µl of chloroform were added. The mixtures were shaken vigorously for 15 seconds and stored on ice for 5 minutes. The samples were then centrifuged at 14,000 rpm for 15 minutes at 4° C. The supernatant was transferred to a new tube containing an equal volume of isopropanol. The tubes were vortexed briefly and centrifuged at 14,000 rpm for 15 minutes at room temperature. The nucleic acid pellets were then washed twice with 70% ethanol and the supernatant from the second wash was aspirated. The pellets were resuspended in a mixture of water (50 µl), 0.1M dithiothreitol (DTT) (1.6 µl), 100 mM Tris/HCl (1.25 µl, ph 7.4) 25 mM MgCl$_2$ (1.0 µl) DNAse 1 (2.5 µ;) (Boehringer Mannheim) and RNAsin (1.25 µl) (Promega, Madison, Wis.) for a final volume of 58.6 µl, then incubated at 37° C. for 60 minutes. Therefore 1×10$^5$ cells=5.8 µl. DNAse was inactivated by incubation at 95° C. for 15 minutes. The RNAs were chilled on ice and 1.5 µl of RNAsin were added before storage at −80° C. For any extractions that were performed on cell pellets larger than 1×10$^6$ cells, the final volume was increased such that the cell concentration remained constant.

Reverse transcription of RNA

RNAs for p53 analysis were diluted to 1×10$^4$ cell equivalents (⅒) in a combination of autoclaved distilled water, 0.1 M DTT and RNAsin to preserve the RNA. The diluted RNAs were divided in half (5000 cell equivalents) for β-actin analysis. All RNAs were subjected to the following reverse transcription (RT) and PCR amplification. Each RNA sample, two 0.5 ml tubes were prepared. One tube was labeled RT+ and one RT−. To each tube, 5.8 µl of diluted sample RNA was mixed with 2.2 µl. of autoclaved distilled water and 4 µl of 2.5 µM 3' oligonucleotide sequence (Seq #2) oligonucleotide sequence. This mix was overlaid with 2 drops of mineral oil for a final volume of 12 µl. A pre-diluted p53 RNA curve (10$^0$–10$^6$ copies) or β-actin curve (10$^1$–10$^3$) was prepared along side the sample RNAs. 2 µl of RNA was used for each curve reaction, and the difference made up with water. The reactions were incubated at 70° C.s for 10 minutes. The RT− tubes, 4 µl of 5×RT buffer and 2 µl 0.1 M DTT, 0.5 µl RNAsin, 0.4 µl 25 mM dNTPs (Promega) and water were added for a total volume of 20 µl. The same reagents were added to the RT+tubes except that 1 µ Superscript II RT (Gibco/BRL) was added to these tubes. The RNAs were incubated at 45° for 60 minutes. The RT was then inactivated by incubation at 95° for 15 minutes. The resultant cDNAs were stored on ice until PCR amplification.

Quantitative PCR of cDNAs

After reverse transcription, each reaction received 80 µl of the following mix: 58.2 µl water. 10 µl of 10× PCR buffer (Perkin Elmer, Norwalk, Conn.), 5 µl each of the 3' and 5' (sequences #1 and #2) 20 µM oligos, 0.8 µl of 25 mM dNTPs and 1 µl of Ta1 polymerase (Perkin Elmer) to a total volume of 100 µl. The reactions were vortexed and briefly centrifuged. The cDNA amplification was performed using these optimized conditions: 95° C.×1 minute, 57° C.×2 minutes (55° C. for β-actin), 72° C.×3 minutes for 30 cycles followed by 72° C.×10 minutes extension to complete unfinished amplifications. The PCR products were stored at −20° C.

Quantitative Analysis of p53 and β-actin PCR products

20 µl of the p53 sample PCR products (2000 cell equivalents) and 10 µl of each serial dilution (10$^0$–10$^5$) of the p53 curve were loaded in triplicate onto 1.5% agarose gels. For the β-actin controls, 10 µl of both samples and the curve were loaded, in triplicate, onto the gels. Electrophoresis was performed for 30 minutes at about 155 volts. The gels were then pressure blotted onto nylon filters for 2 hours. The filters were UV cross-linked, prehybridized in a solution of water, 1.0% SDS, 1× Denhardt's and herring sperm DNA for ½ hour and probed at 150,000 cpm/ml with an internal sequence $^{32}$P end-labeled oligonucleotide. The filters were washed and analyzed on a molecular Dynamics Phosphorimager using ImageQuant software. Image data was stored on magnetic tape. Standard autoradiography was also performed.

Generation of the p53 standard curve:

A 442 nucleotide fragment of the p53 gene obtained from the American Type Culture Collection in Rockville, Md. was cloned into the RNA expression vector pGEM 4Z (Promega). In vitro transcription of the cloned fragment was performed with an SP6 polymerase (Promega). The resulting RNA was quantified spectrophotometrically and copy number deducted by its known transcript length. The RNA was serially diluted to one copy in a diluent designed for RNA preservation (water, 0.1 M DTT, RNAsin). The resulting curve was amplified according to the RT/PCR protocol as described. The curve was proven to be both quantitative and reproducible.

Generation of the β-actin standard curve:

One million PBMCs from a non-infected donor were harvested and separated on ficoll as described above. RNA was isolated according to the previously described RNAzol B protocol. The RNA was serially diluted from 10,000 to 100 cell equivalents and stored at −80° C. in the same buffer as the diluted sample of RNAs. (See β-actin nucleotides above.)

Data analysis:

Quantitation of p53 and β-actin relative phosphor units (RPU) was performed with Excel software (Microsoft, Redmond, Wash.). RPU values from each designated quantitation rectangle on the phosphor image were then transferred to an Excel spreadsheet. Triplicate RPU values for each sample were averaged. Any value within the triplicate was excluded if it failed the Q-test. Averages were then taken from the remaining two values. Conversion of RPU to copy number for p53 and to cell equivalents for β-actin were accomplished using the StatView 4.5 program (Abacus Concepts, Berkeley, Calif.). Regression plots were created using the log of the known RNA copy number vs. the log of the curve RPUs from each experiment. All experiments used to obtain results contained curves with an R$_2$ value >0.,9. The resulting Y-intercept and slope were then used in the equation:

$$\text{copy number}=\text{slope }(x)+y\text{-intercept}$$

to calculate each sample's copy number from the averaged RPU values. The β-actin data was analyzed in identical fashion except the RPU was converted to cell equivalents instead of copy number. The number of cell equivalents loaded onto the gel was then divided by the number quantitated from the curve. This was termed the correction factor. The p53 copy number was corrected for RNA content by multiplying the correction factor by the number of copies calculated by the previous equation. Graphs were generated using Cricket Graph III (Computer Associates, San Jose, Calif.).

Measurement of p53 expression in PBMC after infection with HIV-1 in vitro.

An in vitro infection of fresh, bulk PBMCs from an uninfected donor was conducted to provide a preliminary picture of the relationship between p53 expression, viral replication and apoptosis over the course of an in vivo infection. There was little difference in p53 RNA expression between the mock (90,000 copies/2000 PBMCs) and infected (78,000 copies /2000 PBMCs) populations over the course of infection. The initial calculation of percent apoptosis supported this hypothesis by showing little difference between the mock and infected cultures on day 4 (about 5% each). However, using a highly sensitive flow analytical technique called immunosubtraction, the apoptosis data clearly demonstrated a cumulative frequency difference of greater than 90 on day 4 for the infected cells over the mock cells.

Interestingly, both populations exhibited a dramatic rise in p53 expression from 55 copies on day 2 to 93,2000 copies on day 4. Most importantly, these data pointed to a strong surge in cell death during the initial stages of culture. Flow analysis of the CD4+ T-cell number dropping nearly 50% while the CD8+'s increased in relative proportion by the end of the study. Determination of p24 antigen revealed a maximum value of 14,000 pg/ml on day 8, indicating a strong infection.

The incidental spike in p53 RNA and apoptosis on day 4 followed by a 20 fold increase in p24 from day 0 to day 8 suggest a potential order of events in HIV infection, presumably with increase in p53 occurring first followed closely by apoptosis and then the production of virus from those remaining CD4+ T-cells that were spared. Surprisingly, there was little correlation between p53 infection and HIV infection.

Measurement of p53 expression in fractionated T-cells:

There was greater p53 expression in the CD4+ T-cell infected culture than in the mock culture on every day except day 1. The p53 expression correlated well with apoptosis levels throughout. Within the infected CD4+ population, apoptosis rose 8% every day. In the average population, using uninfected volunteers, the arithmetic mean of p53 expression was found to be substantially lower than the smaller value of any patient subset found within HIV-1 infected cohorts. In general, the progressor p53 expression increased as CD4+ cell counts dropped and vice versa.

The data indicated a positive association between p53 expression and HIV disease progression when two widely accepted parameters, CD4+ T-cell number and serum viral burden were used. It was found that p53 expression, driven by immune response, can lead to viral load reduction and points to an order in HIV-1 pathogenesis. Hence, the use of the novel method of the invention provides means of monitoring and predicting the progression of disease.

What is claimed is:

1. A composition of matter containing at least one of the following sequences:

5'-CAT CTA CAA GCA GTC ACA-3' (SEQ ID NO:1)

5'-GCA GTG CTC GCT TAG TGC-3' (SEQ ID NO:2)

5'-ATT CAC TAC AAC TAC ATG-3' (SEQ ID NO:3)

in an aqueous carrier.

2. A composition containing at least one of the following sequences:

```
5'-ATC ATG TTT GAG ACC CTT CAA-3'                      (SEQ ID NO:4)
5'-CAT CTC TTG CTC GAA GTC CA-3'                       (SEQ ID NO:5)
5'-GAC CTG GCT GGC CCG GAC CTG ACT GAC TAC TAC-3'      (SEQ ID NO:6)
``` in an aqueous carrier.

3. At least one sequence chosen from among sequences of the formulas:

```
5'-CAT CTA CAA GCA GTC ACA-3'                          (SEQ ID NO:1)
5'-GCA GTG CTC GCT TAG TGC-3'                          (SEQ ID NO:2)
5'-ATC CAC TAC AAC TAC ATG-3'                          (SEQ ID NO:3)
5'-ATC ATG TTT GAG AC CTT CAA-3'                       (SEQ ID NO:4)
5'-CAT CTC TTG CTC GAA GTC CA-3'                       (SEQ ID NO:5)
5'-GAC CTG GCT GGC CCG GAC CTG ACT GAC TAC TAC-3'.     (SEQ ID NO:6)
```

4. A method of determining the level of tumor suppressor gene p53 comprising the steps of:

(1) performing reverse transcription of a sample of p53 mRNA to prepare a mix containing dNTPs and the 3' p53 oligonucleotide, (2) adding to the product of step (1) additional dNTPs and 5' p53 oligonucleotide, (3) subjecting the product obtain in step (2) to varying temperatures to provide for elongation, (4) applying the product of step (3) to gels, (5) blotting said gels obtained in step (4) onto filters, (6) prehybridizing the product of step (5), and (6) probing with a labelled internal oligonucleotide specific for a sequence of the p53 sequence and measuring the results against a β-actin RT-PCR curve which has been standardized for cell number to determine the level of p53 in the sample.

\* \* \* \* \*